(12) United States Patent
Bolorforosh et al.

(10) Patent No.: US 6,673,016 B1
(45) Date of Patent: Jan. 6, 2004

(54) ULTRASOUND SELECTABLE FREQUENCY RESPONSE SYSTEM AND METHOD FOR MULTI-LAYER TRANSDUCERS

(75) Inventors: Mirsaid Bolorforosh, Portola Valley, CA (US); Todor Sheljaskow, Issaquah, WA (US); Stephen R. Barnes, Bellevue, WA (US); Peter Guo, Woodinville, WA (US); Sevig Ayter, Cupertino, CA (US); Timothy L. Proulx, Santa Cruz, CA (US); Amin M. Hanafy, Los Altos Hills, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/076,688

(22) Filed: Feb. 14, 2002

(51) Int. Cl.[7] .................................................. A61B 8/00
(52) U.S. Cl. ........................ 600/437; 600/447; 600/459
(58) Field of Search ................................. 600/459, 437, 600/439, 462–471; 128/916; 345/173; 310/334–336, 328, 314, 366, 368, 365, 316.01; 73/642, 644, 609, 625, 626; 29/25.35

(56) References Cited

U.S. PATENT DOCUMENTS

| 5,415,175 | A | 5/1995 | Hanafy et al. |
| 5,438,998 | A | 8/1995 | Hanafy |
| 5,548,564 | A | 8/1996 | Smith |
| 5,625,149 | A | 4/1997 | Cururaja et al. |
| 5,675,554 | A | 10/1997 | Cole et al. |
| 5,685,308 | A | 11/1997 | Wright et al. |
| 5,690,608 | A | 11/1997 | Watanabe et al. |
| 5,744,898 | A | 4/1998 | Smith et al. |
| 5,957,851 | A | 9/1999 | Hossack |
| 5,989,869 | A | 11/1999 | Filippini et al. |
| 6,005,827 | A | 12/1999 | Hossack et al. |
| 6,104,670 | A | 8/2000 | Hossack et al. |
| 6,390,985 | B1 | * 5/2002 | Mamayek .................... 600/459 |
| 6,429,574 | B1 | * 8/2002 | Mohr et al. .................. 310/334 |

OTHER PUBLICATIONS

John A. Hossack, Student Member, IEEE, and Bertram A. Auld, Fellow, IEEE, "Improving the Characteristics of a Transducer Using Multiple Piezoelectric Layers," IEEE Transactions on Ultrasonics, Ferroelectrics, and Frequency Control, vol. 40, No. 2, p. 31–139, Mar. 1993.

T.R. (Raj) Gururaja, Abraham Shurland, and Jie Chen, "Medical Ultrasonic Transducers With Switchable Frequency Bands Centered About F and 2F," 1997 IEEE Ultrasonics Symposium, p. 1659–1662, 1997.

* cited by examiner

Primary Examiner—Ali M. Imam (57) ABSTRACT

A transducer system and method for harmonic imaging is provided. At least one transducer element is provided. The transducer element comprises two or more stacked piezoelectric layers. Information from each of the layers is independently processed during one of a transmit event, a receive event, and both transmit and receive events. Information from the transducer element is provided to a filter. The filter isolates harmonic information for imaging. By providing a multi-layer transducer element with independent processing for each layer, a wide bandwidth transducer for harmonic imaging is provided. The null associated with most transducers at the second harmonic of a fundamental frequency is removed or lessened.

42 Claims, 9 Drawing Sheets

ULTRASOUND SELECTABLE FREQUENCY RESPONSE SYSTEM AND METHOD FOR MULTI-LAYER TRANSDUCERS

BACKGROUND

This invention relates to a medical diagnostic ultrasound transducer system and method. In particular, a transducer system providing increased bandwidth for imaging with different frequencies is provided.

Acoustic energy is transmitted into a patient at fundamental transmit frequencies. Acoustic energy is reflected off of tissue, fluid or other structures within the patient. The reflections include energy at the fundamental frequency band as well as energy generated at harmonic frequencies of the fundamental frequency band. The transducer converts the acoustic energy into an electrical signal.

Transducer bandwidth may limit the actual response, reducing the information content at harmonic or other frequencies. Manufacturing transducers with a 6 dB bandwidth or better exceeding 80% of the desired frequency range is difficult and expensive. For harmonic imaging, a 6 dB bandwidth exceeding 100 or 140% is preferably provided. For example, the transducer may transmit energy in a 3 to 5 MHz frequency range and receive information of interest in the 6 to 9 MHz range.

Larger bandwidth transducers are generally desirable for any type of ultrasonic diagnostic imaging. For example, transducers with a wide bandwidth are used for obtaining information at different fundamental frequencies during a same or different imaging sessions. Various techniques have been suggested for providing wide bandwidth transducers. For example, T. R. Gururaja et al in 'Medical Ultrasonics Transducers With Switchable Frequency Bands Centered about $f_0$ and $2f_0$', 1997 IEEE Ultrasonic Symposium, pp. 1659–1662, disclose an electrostrictive transducer element using two layers. A selected bias is applied to one layer, and a transmit waveform is applied to an electrode between the two layers for wide bandwidth transmission. As another example, J. Hossack et al. in Improving the Characteristics of A Transducer Using Multiple Piezoelectric Layers, IEEE Transactions On Ultrasonics, Ferroelectrics and Frequency Control, Vol. 40, No. 2, March 1993, disclose a two-layer piezoelectric single element transducer. A different waveform is applied to each of the layers on transmit, and phasing or delays are applied to signals from one of the layers relative to another layer on receive. As another example, different materials in a single layer transducer element may be used to extend the frequency range of the transducer.

U.S. Pat. No. 5,957,851, the disclosure of which is incorporated herein by reference, discloses an ultrasound transducer with multiple piezoelectric layers for use in harmonic imaging. Diodes or a transistor is used to isolate one layer from the other during transmit or receive. The same transducer is used to transmit at a fundamental frequency and receive at a harmonic frequency. For this passive switching system, the same transmit and receive processing is performed for each layer when each layer is being used.

Transducer bandwidth is also important for different types of imaging modes, such as Doppler and B-mode imaging. For B-mode imaging, the highest frequency possible is used for tissue close to the surface and lower frequencies are used for tissue deeper or further away from the transducer. A dual frequency transducer covers a much wider range of frequencies than previously possible using conventional transducer designs. For example, a dual frequency transducer covers a frequency spectrum with an effective −6 db bandwidth of 120%–130% of the operating center frequency. However, the conventional transducer designs can only obtain 75%–95% bandwidth. For the color flow and Doppler modes of imaging, the transducer can operate over a much wider frequency band to result in better signal penetration or a wider frequency band for the detection of the Doppler frequency shift.

BRIEF SUMMARY

The present invention is defined by the following claims, and nothing in this section should be taken as a limitation on those claims. By way of introduction, the preferred embodiments described below include a method and transducer system for selectable frequency imaging. At least one transducer element is provided. The transducer element comprises two stacked piezoelectric layers. The layers are stacked in the height or thickness direction which is perpendicular to an elevation-azimuth plane (i.e. azimuth is X direction, elevation is Y direction and range is Z direction). Information from each of the layers is independently processed during one of a transmit event, a receive event, and both of transmit and receive events by applying relative delays and/or amplitude changes between the layers. The frequency response of the bi-layer transducer element is adjusted as a function of the delay and amplitude control, controlling the operation frequency and/or increasing the impulse-echo bandwidth or effective bandwidth of the transducer. The frequency response of the bi-layer transducer element is modified by interference so that the signals for each layer constructively interfere in the frequency region of the desired peak response. Alternatively, destructive interference is created in a frequency band to be suppressed.

In a first aspect, each of the layers of the transducer element comprise a material with different acoustic properties and transfer characteristic, such as one layer of solid ceramic material and the other layer of piezo-composite material. Using relative delay and/or amplitude adjustments, the different transmit or receive processing accounts for the different acoustic transfer characteristics, providing selectable frequency appropriate interference.

In a second aspect, a matching layer of the transducer element varies as a function of elevation across the element. For example, varying the thickness or grading provides for lower frequency operation at the edges of the elevation aperture and higher frequency operation at the center of the elevation aperture.

In a third aspect, a multiplexer selectively operates the transducer element in different resonance frequency modes. For example, a single transmit and/or receive system channels selectively connect with one or more of electrodes between layers, on top of the element or below the element. The transducer element is operated for receiving at the same frequency as the transmit frequency or receiving at a different frequency than the transmit frequency.

Further aspects and advantages of the invention are described below in conjunction with the preferred embodiments.

DETAILED DESCRIPTION OF THE PREFERRED EMBODIMENTS

Transducer systems and methods for imaging with a bi-layer transducer are discussed below. One or more of the transducer elements comprises multiple layers of piezoelectric material. During one or both of transmit and receive events, independent processing is provided for each of the layers. For example, a different waveform is provided to each of the layers of the transducer element during the transmit event. As another example, one of the electrical signals is delayed relative to another during the receive event. The independent processing provides for an increased bandwidth of the transducer.

Figure 1:
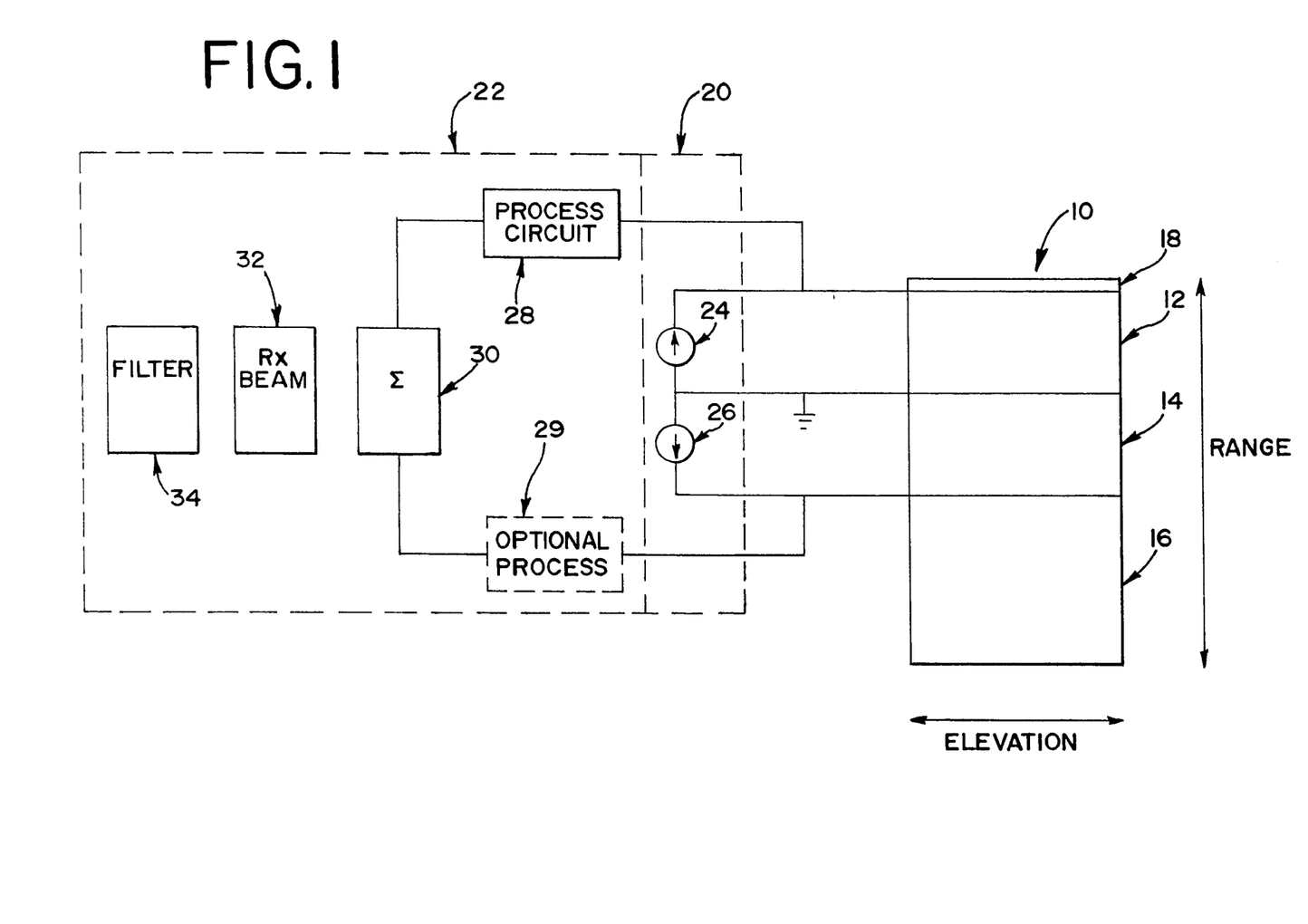
FIG. 1 is a block diagram of one embodiment of a medical diagnostic ultrasound transducer system.
Figure 2:
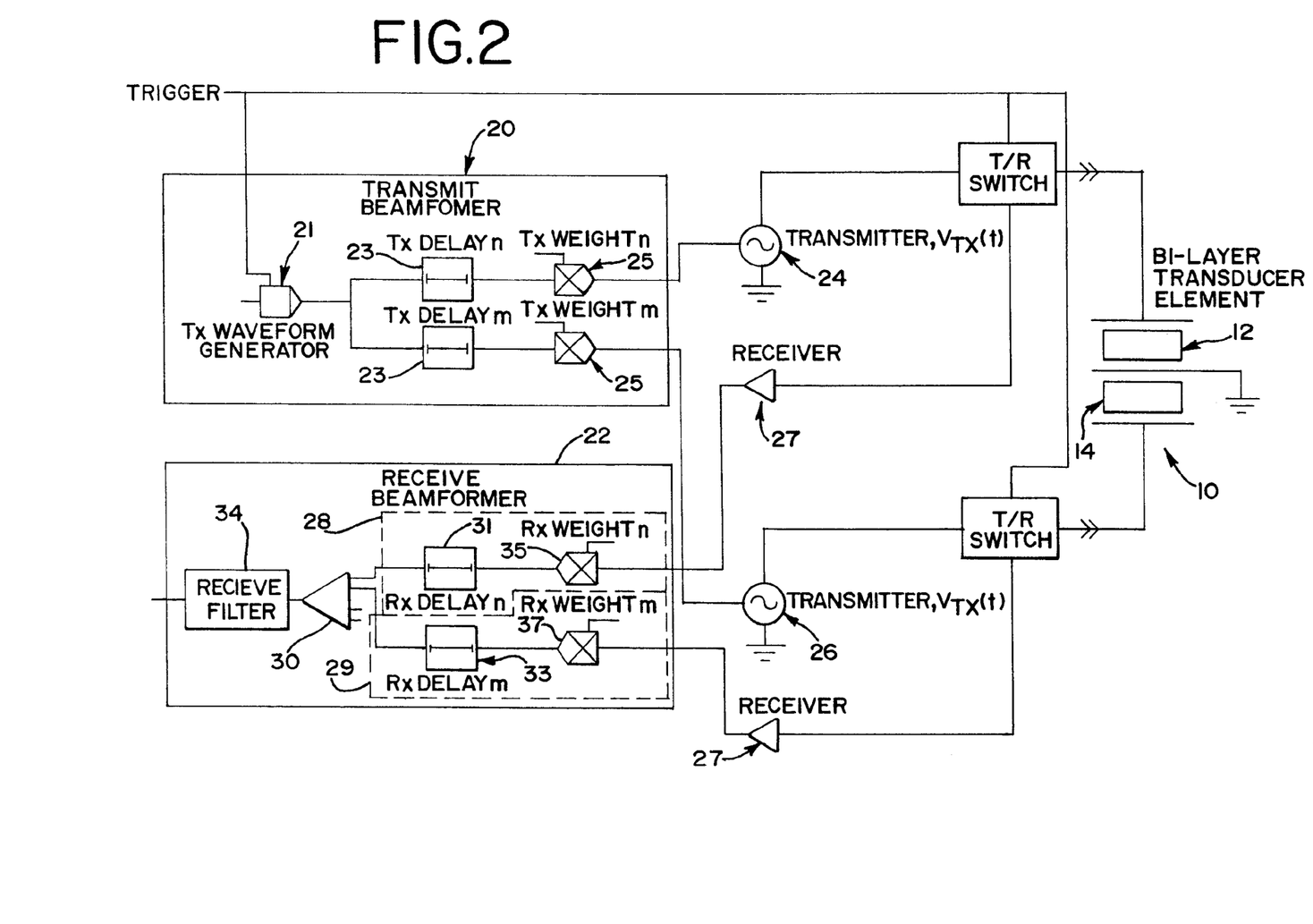
FIG. 2 is a block diagram of another embodiment of a medical diagnostic ultrasound transducer system.

FIGS. 1 and 2 show block diagrams of ultrasound transducer systems for harmonic or fundamental imaging. The transducer system of FIG. 1 comprises a transducer element 10 connected with a transmitter 20 and a receiver 22. A different element may be connected with the transmitter 20 than is connected with the receiver 22.

The transducer element 10 comprises a top layer 12 and a bottom layer 14 of piezoelectric material, both layers between a backing layer 16 and a matching layer 18. The top and bottom layers 12 and 14 comprise a same or different piezoelectric material, such as a PZT/epoxy composite, a PVDF ceramic, Motorola HD3303, PZT 5H, or other piezoelectric material or ceramic. In alternative embodiments, the piezoelectric material comprises electrostatic micromachined devices, such as an electrostatic moving membrane device. Each of the layers 12, 14 has a same or different geometry. For example, the same thickness is used for each layer, such as a ½ mm thickness. Other thicknesses may be used, including thicknesses that vary in one or more dimensions.

In one embodiment, the top and bottom layers 12, 14 comprise different transducer materials. For example, the top layer 12 comprises a solid piezoelectric material, such as a solid ceramic or electrostatic substrate. The solid piezoelectric material is free of epoxy or free from kerfs for each transducer element. The bottom layer 14 comprises piezo-composite material, such as a combination of piezoelectric ceramic and epoxy or polymer. Piezo-composite materials include piezoelectric material beams separated by epoxy filled kerfs in one dimension or piezoelectric material posts separated by epoxy filled kerfs in two dimensions, but other piezo-composites may be used.

In one example embodiment, the top layer 12 comprises a piezo-composite having 14–19 Mrayl acoustic impedance, and the bottom layer comprises a solid piezoelectric material having about 30 Mrayl acoustic impedance. The top and bottom layers 12, 14 are also characterized by different transfer functions for acoustic energy. The substantially different transfer functions are accounted for by the independent processing (e.g. altering relative phase and/or amplitude of signals for each layer) discussed herein. Greater differences in the materials and associated transfer functions for the top and bottom layers 12, 14 may provide greater bandwidth and sensitivity.

As another example of different materials, the top layer 12 comprises a piezo-composite material and the bottom layer 14 comprises a solid piezoelectric material. Other combinations of different materials may be used. The transducer element 10 is well matched by the matching layer 18 and the backing block 16. For example, the backing block 16 comprises tungsten-loaded epoxy or another backing block material. For example, other backing materials comprise various one of or combinations of metals (e.g., lead, copper), metal oxides (e.g., lead oxide, tungsten oxide), glass microballoons or spheres in a polymer, such as neoprene, polyurethane or epoxy.

The matching layer 18 comprises a double matching layer comprising a high impedance matching layer (e.g., acoustic impedance about 9–10 MRayl) next to the top layer 12 and a low impedance matching layer (e.g., acoustic impedance about 2–2.5 MRayl) spaced away from the top layer 12 by the high impedance matching layer. Single or triple matching layers are also possible. The matching layer 18 may be absent. Given the broad bandwidth of the transducer element 10, the matching layer 18 may be selected as a function of higher frequencies (i.e. thinner rather than thicker). For example, the thickness of the matching layer 18 is less than the wavelength divided by four for the highest operating frequency of the transducer element 10. The bond layers between transducer components are thin and uniform.

In one embodiment, the matching layer 18 varies in an acoustic impedance characteristic along one dimension to provide a gradual change in the frequency response of acoustic impedance matching layer across the transducer element 10. The variation in acoustic impedance allows operation over a wider bandwidth than a matching layer 18 with no variation. The amount of variation provides for efficient operation at different frequencies, such as a lower fundamental transmit frequency and a higher second order harmonic frequency of the fundamental frequency or other relative frequencies. The variation in the matching layer 18 provides similar bandwidth as variation in piezoelectric material as disclosed in U.S. Pat. Nos. 5,415,175 and 5,438,998, the disclosures of which are incorporated herein by reference. The variation is along the elevation aperture of the transducer element 10, but may be along more than one dimension or a different dimension. Different gradual or stepped variations or variation techniques alone or in combination may be used. One matching layer 18 provides the variation, but more than one matching layer 18, such as both layers of a double matching layer 18, may have a varied acoustic impedance.

In one example of variation in the matching layer 18, the thickness of the matching layer 18 varies along the elevation dimension of the transducer element 10. A thicker matching layer 18 at the edge portion of the transducer element 10 matches to or provides operation at a lower frequency. A thinner matching layer 18 at the center of the transducer element matches to or provides operation at a higher frequency. The thickness gradually varies across the aperture, such as along a Gaussian or parabolic curve. Other variations in thickness and associated acoustic impedance may be used.

As another example, the matching layer 18 is graded for operation over a wide frequency band. The density and the acoustic impedance of the matching layer 18 varies along the longitudinal axis (i.e., axis normal to the plane of the transducer surface). In one embodiment, the matching layer 18 includes two materials, each associated with a different acoustic impedance and corresponding frequency bands of operation. The acoustic impedance varies by distribution of the two materials along the longitudinal axis (e.g., elevation dimension). For example, one matching layer material is patterned or etched to provide apertures, divots, indentions or other locations for depositing the second matching layer material. The size, number or distribution of the deposits varies gradually along the elevation dimension. The distribution density of the first material is greater at the interface with the piezoceramic layer and the distribution density of the material is gradually reduced from the interface with tissue or the lens material. As yet another example, the matching layer 18 is patterned along one dimension. Different patterns providing different thickness across the aperture increase the bandwidth. In one embodiment, the matching layer 18 has a triangular pattern across the elevation aperture of the transducer element. None, one or more other matching layers with or without patterns may also be provided with the patterned matching layer. The pattern causes the acoustic impedance of the entire matching layer 18 to vary as a function of elevation position. Other repeating or non-repeating patterns may be used.

FIGS. 1 and 2 show two embodiments of transducer elements 10 and associated signal paths. A plurality of the transducer elements 10 are used in an array. The waves output by the transducer elements 10 either in transmit or receive are separately delayed and apodized relative to each of the elements 10. The separate waveforms are then summed to generate a receive beam.

The transmitter 20 connected with the element 10 comprises first and second sources 24 and 26 of waveforms. Each or both sources 24 and 26 comprise an analog or digital transmit beamformer channel. For example, beamformers disclosed in U.S. Pat. Nos. 5,675,554, 5,690,608, 6,005,827, or U.S. Pat. No. 6,104,670, the disclosures of which are herein incorporated by reference, are used. Other sources of waveforms may be used, such as waveform generators or a waveform memory, digital-to-analog converter and amplifier. In alternative embodiments, a single source 24, 26 of waveforms is provided, and a delay or filter alters the waveform applied to one of the layers 12, 14 with respect to a waveform applied to the other layer 12, 14. Independent processing of the waveform is provided for the top layer 12 and for the bottom layer 14. Waveforms with different characteristics are applied to each layer 12, 14, but a same waveform may be applied in some situations.

The block diagrams of FIGS. 1 and 2 use two system channels for one transducer element 10 for a dual frequency mode of operation. Alternatively, the three electrodes connected to each transducer element 10 are configured using a series of switches so that each transducer element 10 can also operate as a transducer element with two layers where only one system channel is required to operate each transducer element (see FIG. 1) in a single frequency mode.

As shown in FIG. 2, the transmitter 20 includes a waveform generator 21 connected with one or more (two as shown) transmit waveform signal paths or transmit beamformer channels having a delay 23 and an amplifier 25. The amplifier 25 alternatively comprises a filter or other device for weighting an amplitude of the transmit waveform. The weights comprise positive or negative weights for amplifying or dividing the amplitude of the received signals. In alternative embodiments, a different waveform generator 21 is provided for each transmit waveform signal path.

The output of the transmitter 20 is provided to the first and second sources 24 and 26 of waveforms. The sources 24 and 26 comprise digital-to-analog converters. Alternatively, the transmit waveform signal paths comprise analog signal paths that include the sources 24 and 26. The delays 23 and amplifiers 25 apply relative delays and/or amplitude weighting to alter the transmit waveform applied to one of the layers 12, 14 relative to the transmit waveform applied to the other layer 14, 12. This independent processing of the transmit waveforms accounts for the different transfer functions associated with different acoustic energy propagation through and boundary for one or more layers 12, 14 of the elements 10.

The receiver 22 connected with the layers 12, 14 comprises a process circuit 28 connected to one of the layers and a summer 30, a receive beamformer 32 and a filter 34 operatively connected with the first and second layers 12 and 14. The receiver 22 comprises analog components, digital components or combinations thereof. The receiver 22 is preferably protected by standard diode clamping circuitry. This limits the voltage at the receiver input terminal to a safe level. Additionally, diode isolation circuitry is preferably included in the transmit circuitry which conducts during transmit events, but provides an open circuit during receive events, isolating the transmitter source impedance. The responses of the two transducer layers 12 and 14 are preferably pre-amplified separately by amplifiers 27. The second transducer layer 12 may be isolated from the first transducer layer 14 by a diode transistor, back-to-back diodes, or other combination of switches which are "on" when an applied voltage exceeds the diode 'turn on' voltage (e.g., about 0.7 volts). Other or no clamping circuitry, pre-amplification and isolation circuitry may be used.

In one embodiment, the process circuit 28 and summer 30 of the receiver 22 are incorporated into the housing of a transducer, reducing cable costs and improving signal quality. Other components may be incorporated into the transducer housing.

The process circuit 28 comprises an analog or digital delay 31. For delaying digital data, the process circuit 28 comprises registers and counters, but may comprise a processor or other digital device. The process circuit 28 has a fixed or programmable amount of delay. For simplicity, a fixed delay is used where the transducer 10 has a known propagation delay from the first layer 12 to the second layer 14. The amount of delay depends on the propagation delay of ultrasound from the first layer 12 to the second layer 14.

In one embodiment, the response of one layer 12, 14 is inverted (e.g., a phase rotation of 180 degrees) while the response of the other layer 14, 12 is non-inverted. Inverting and non-inverting pre-amplifiers are known. As an example, common in-phase signals are applied during a transmit event to both layers, and a strong response at the fundamental is obtained when the piezo-cermaic poling orientations for the first and second layers 12, 14 are along the same direction. During the receive event, the response of one layer is inverted prior to summing (i.e. subtraction), and consequently, a strong second harmonic response is obtained. By delaying to compensate for the propagation delay of ultrasound from the first layer 12 to the second layer 14, and inverting the signal from the first layer 12, a strong second harmonic signal is obtained with wide frequency bandwidth.

In the context of this application, phase and delay are used interchangeably. A delay corresponds to a linearly varying phase as a function of frequency. The phase function applied may be frequency dependent or frequency independent. As shown, the process circuit 28 connects with the top layer 12, and no delay or a different delay 33 connects with the bottom layer 14. Information from the top layer 12 and the bottom layer 14 are independently processed. The responses of the two layers are summed after the relative delay or phasing (independent) processing and are then treated as one response (FIG. 1) or are summed as part of the receive beamforming process on two different receive system channels (FIG. 2). In alternative embodiments, a delay is provided for both the top and bottom layers 12 and 14, as shown by an optional process circuit 29. Other components, such as filters, processors or analog circuitry may be used on one or both of the separate data paths from the top and bottom layers 12 and 14 to provide independent processing. The independent processing may provide a same process or delay in some situations, but typically provides for a different process as described below.

In addition or as alternatives to the delays 31, 33, amplifiers 35, 37 apply relative weighting to the signals from each layer 12, 14 of the transducer element 10. Alternatively, the amplifiers 35, 37 comprise filters for weighting the amplitude of the received signals. The weights comprise positive or negative weights for amplifying or dividing the amplitude of the received signals. The relative weighting accounts for the amplitude effects of the different propagation paths from and boundary conditions for each layer 12, 14. Weighting provides control over the amount of constructive and destructive interference of the acoustic waveforms from each layer 12, 14 given the different transfer functions of the layers 12, 14. In yet other alternative embodiments, the process circuits 28 and 29 comprises complex filters for altering the received signals from one layer 12 relative to the other layer 14 to account for the difference in transfer functions.

The summer 30 receives the delayed information and comprises an analog or digital summer. For example, an operational amplifier is used for analog information, or a digital summation circuit is used for digital summation. Summing may occur, depending on implementation, in the analog or digital domain. If in the analog domain, the summer 30 may comprise a wire junction combining the currents from both layers. Other devices for combining the independently processed information from each of the layers 12 and 14 may be used, such as a summer also used to sum signals from multiple channels in a receive beamformer. The summer 30 comprises a summer prior to receive beamformation (FIG. 1) or a summer for combining information from different channels as part of receive beamformation (FIG. 2).

The receive beamformer 22 comprises analog and/or digital components. For example, the receive beamformer disclosed in U.S. Pat. No. 5,685,308, the disclosure of which is incorporated herein by reference, is used. The disclosed receive beamformer includes the filter 34, summer 30 and process circuits 28, 29 for the embodiment of FIG. 2. In alternative embodiments, the filtering function and the receive beamformer function are performed with separate components. Other receiver components, such as the summer 30 and/or process circuit 28, may be separate from the receive beamformer 22 (FIG. 1).

The optional filter 34 receives the beamformed data and comprises a digital signal processor, an application specific integrated circuit (ASIC), a finite impulse response filter, an infinite impulse response filter or other analog and/or digital components. In one embodiment, the filter 34 is included as part of the receive beamformer 32. The filter 34 provides highpass, bandpass, lowpass or spectral whitening response. The filter 34 passes information associated with the desired frequency band, such as the fundamental transmit frequency band, a harmonic of the fundamental frequency band or any other desired frequency band. As used herein, harmonic comprises higher harmonics (e.g., second, third, . . . ), fractional harmonics (3/2, 5/3, . . . ), or subharmonics (1/2, 1/3, . . . ). The filter 34 may comprise different filters for different desired frequency bands or a programmable filter. For example, the filter 34 demodulates the signals to base band. The demodulation frequency is programmably selected in response to the fundamental center frequency or another frequency, such as a second harmonic center frequency. Other center frequencies may be used, such as intermediate frequencies. Signals associated with frequencies other than near the base band are removed by low pass filtering.

As an alternative or in addition to demodulation, the filter 34 provides band pass filtering. The demodulated and/or filtered signal is passed to an ultrasound signal processor as complex in-phase and quadrature signals, but other types of signals, such as radio frequency signals, may be passed.

The above described transducer systems are used during one of a transmit event, a receive event or combinations thereof. In one embodiment, programmed excitation waveforms are independently processed and applied to each of the top and bottom layers 12 and 14 during a transmit event, and a different delay and/or amplitude weight is applied to information received from each of the top and bottom layers 12 and 14 for independent processing during a receive event. Alternatively, information from a single layer is obtained during the receive event, or a single layer is used during a transmit event. In other alternative embodiments, switching mechanisms are provided to allow use of two layers during a transmit or receive event using a same process, such as applying a same transmit waveform to the top electrode of the top layer 12 and the bottom electrode of the bottom layer 14 and grounding the center electrode.

Due to the different acoustic loading of the first and second layers 12, 14, the transfer functions are different for both of transmit and receive operation. If the first and second layers 12, 14 have different piezoelectric, acoustic or electrical loading conditions, different transfer functions result. The transmit waveforms applied to each layer 12, 14 are optimized to obtain constructive or destructive interference of the pressure waveforms emitted by each layer 12, 14 for optimum operation at the desired frequency. The received signals are altered to account for the different transfer functions. Optimization of the signals allows for operation at different frequencies, such as transmitting at a fundamental frequency and selectively receiving at the fundamental frequency or a harmonic frequency of the fundamental frequency. Optimization by alteration of relative amplitudes, delays and/or pulse shape provides waveforms with a similar amplitude and phase at the face or emitting surface of the element 10 for maximum constructive interference with minimal noise at other frequencies.

For transmit events, the two layers 12, 14 may be operated in parallel or without independent processing, since the bandwidth of interest is limited to the fundamental frequency. As used herein, independent processing comprises at least one component or act provided for one of the layers that is independent of a component or act being provided for another of the layers. The independent processing may be responsive to information from another layer.

In one embodiment, the independent processing applies a phase alteration to information to or from the top and bottom layers 12, 14. The phase of information for one layer is altered with respect to the phase of the other layer. The phase function is frequency dependent but may be independent of frequency. In transmit, the waveforms applied to each layer are in-phase or slightly out of phase (e.g., 90°). Generally, the received harmonic signal is substantially out of phase (e.g., around 180°) and therefore different phasing is used to obtain a meaningful response.

During transmission at fundamental frequencies, phased shaped waveforms are generated by the sources 24, 26 to produce the desired low frequency acoustic wave output by the transducer element 10. Alternatively, a high frequency waveform is output for using subharmonics, the fundamental frequency, and/or a frequency for color flow or spectral Doppler imaging.

The transducer element 10 may be represented as an equivalent circuit with two voltage sources, one for each layer 12, 14. The output of the transducer element 10 is obtained from the sum of the two sources. This is an application of the current superposition theorem. The relative phase and amplitude of the two sources 24, 26 is measured for all frequency points of interests and then compensated for during transmission. During the transmission, the phase and amplitude off-set due to the different propagation path from each layer 12, 14 cancels the applied phase and amplitude, and the maximum output is obtained at all desired frequencies.

Using a mathematical representation, suppose the output of a top layer is a phaser with a phase value of $\theta_1$ having a unit length, and the output of the second layer is a phaser with a phase value of $\theta_2$ also having a unit length. If the difference between $\theta_2$ and $\theta_1$ is applied to the input of the first layer, an in-phase output of two unit lengths is provided. As described by Hossack et al. in Improving the Characteristics of A Transducer Using Multiple Piezoelectric Layers, IEEE Transactions On Ultrasonics, Ferro Electrics, and Frequency Control, Vol. 40, No. 2, March 1993 (the Hossack article), there is no unique solution for the waveforms to apply to each of the layers 12, 14 for obtaining a specified output response. In one embodiment, the waveforms requiring the smallest input amplitudes are used.

The force F of the output is obtained from the particle displacement, $A_F$. $F=sZ_F A_F$, where s is the Laplace operator and $Z_F$ is the mechanical impedance. In the Laplace domain for the multiple layer system, $\overline{F}=\overline{\beta}_1\overline{V}_1+\overline{\beta}_2\overline{V}_2+\overline{V}_1\ldots+\overline{\beta}_N\overline{V}_N$, where N is the number of layers and $\beta_1$ is the transfer function between the applied voltages and the output, and V is the applied voltage. $\beta_1$ may be obtained by measuring the force F when $V_1$ is set to 1 and $V_2$ is set to 0. $\beta_2$ may be evaluated similarly. Assuming the voltages applied to each layer are equal in terms of magnitude for a two-layer transducer and equal to unity (i.e. 1), $\overline{F}=\overline{\beta}_1+\overline{\beta}_2$ or the $|F|\angle\theta=|\beta_1|\angle\theta_1+|\beta_2|\angle\theta_2$. The force output the absolute value of $F\angle\theta$ is maximized if $\theta_2=\theta_1$ as described above. The phase angle of $V_2$ is adjusted to compensate for the phase difference between $\beta_1$ and $\beta_2$. The desired result is obtained by setting $V_2=V_1\angle(\theta_1-\theta_2)$. The time domain excitation functions $V_1(t)$ and $V_2(t)$ are obtained using an inverse Fourier transform. As described in the Hossack article, once the desired acoustic output waveform is defined (e.g. a compact Gaussian pulse) and the transfer function (voltage in to pressure out) of the dual layer transducer established, the required voltage excitation functions to obtain the desired pulse shape are determined. In the Laplace (or Fourier) domain, the required output function is divided by the transfer function. Hence, the required value for $V_1$ is determined. $V_2$ is identical to $V_1$ except that the phase angle $(\theta_1-\theta_2)$ is applied. See pages 134–135 of the reference. In one embodiment, the phase angle correction is performed as a function of frequency. The phase angle correction may be linear as a function of frequency, corresponding to a simple time delay. Alternatively, the actual or an approximate non-linear function is used.

For a transducer where the piezoelectric ceramic layer thickness is non uniform as described in U.S. Pat. No. 5,415,175 to Amin Hanafy, the time delay can be variable depending on the desired operating resonance frequency. In this case, the operating frequency and the time delay are a function of the piezocermic layer thickness.

The independently generated or processed waveforms are provided to respective ones of the layers 12, 14 of the transducer element 10. In response, the transducer element 10 generates an acoustic waveform. The acoustic waveform propagates into the body, interacting with tissue and fluid and giving rise to harmonic information. Echo signals, including the harmonic signals and signals at the fundamental frequency, propagate back to the transducer element 10.

In the receive event, the top and bottom layers 12 and 14 generate electrical signals in response to the acoustic echoes. The information from each of the two layers 12, 14 is phase and amplitude corrected and added. Since the relative phase and amplitude characteristics of the layers 12, 14 are known, the frequency dependent phase and amplitude difference between the signals is applied as a phase and amplitude correction to one or both of the signals from the top or bottom layer 12, 14. After the delay or phase is adjusted, the information from the two layers is summed. In one embodiment, the process circuit 28 provides a fixed delay and/or amplitude. Alternatively, a dynamic delay and/or amplitude are used. Additionally, the phase function may be dynamic or fixed. The phase function is different during receive events than the applied transmit function, such as inverting the signal.

Where second harmonic information is of interest, the delay is preferably applied to information from the top layer 12. In alternative embodiments, the delay is applied to the information from the bottom layer 14 or a combination of layers 12, 14. The amount of delay preferably corresponds to the sound propagation speed from the center of the top layer 12 to the center of the bottom layer 14 (e.g. typically equivalent to the propagation delay through one complete layer where both layers 12, 14 are equally thick). Since propagation speed is sometimes frequency dependent due to the finite transducer element dimensions relative to a wavelength, the process circuit 28 may provide delay as a function of frequency.

As described in the article by Hossack et al. referenced above, the phase relationship between the information from the two layers 12, 14 for receive events is the same or similar to the phase relationship between the two layers 12, 14 for transmit events. Since the response closely resembles the time delay function corresponding to the transmit time through the layers, the approximation may be used for applying an effective delay. Alternatively, for lower cost and somewhat lesser performance, a fixed phase inversion is applied to one of the layers. Application of the independent processing delay and summation of the information from the two layers provides a higher peak sensitivity and a bandwidth without a null at the second harmonic.

Figure 3A:
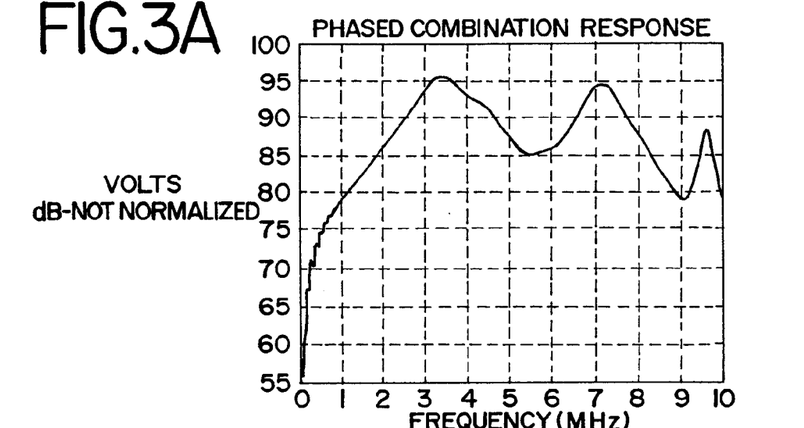
FIGS. 3A through 3C are graphical representations of a transducer spectral response for a multiple layer transducer, a top layer of the transducer, and a bottom layer of the transducer, respectively, of the transducer system of FIG. 1.
Figure 3B:
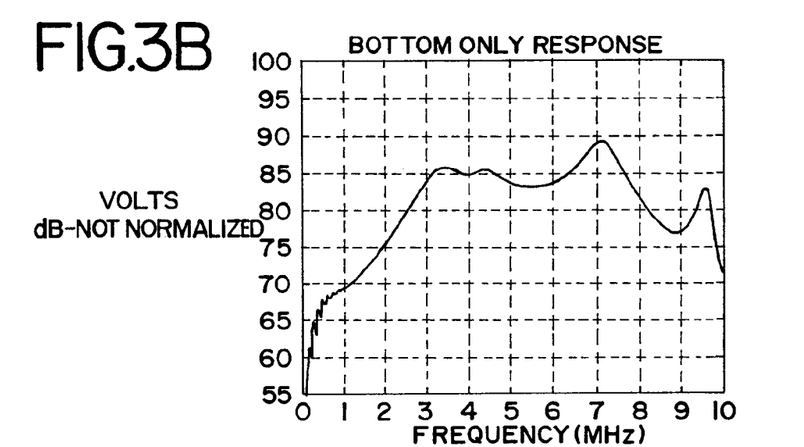
Figure 3C:
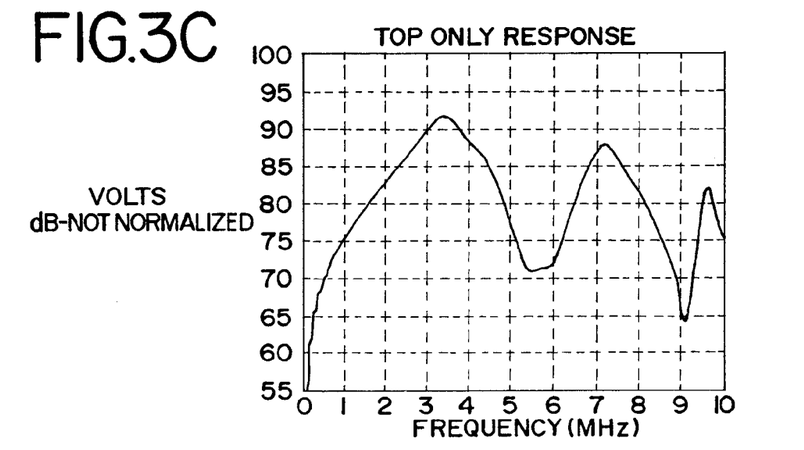

The information from each of the transducer layers 12, 14 is summed by the summer 30. The resulting sum provides for wide bandwidth information. FIG. 3A represents the spectral response of the independently processed and combined information using the system of FIG. 1. The response peaks at around 95 dB at 3⅓ MHz and around 7 MHz where the dB scale is offset as a result of the Fourier transform step. The dip between these two frequencies may be reduced as a function of the design of the transducer, including layer thickness, materials and geometry. For example, a lower impedance piezoelectric material is substituted, such a piezoelectric ceramic/epoxy composite for a pure piezoelectric ceramic material, and a heavier backing material may be used. FIGS. 3B and 3C represent the spectral response of the bottom and top layers 12, 14, respectively. As shown, a lesser magnitude is provided.

FIGS. 6 through 10 represent the impulse-echo two-way (i.e. transmit and receive) response of the bi-layer transducer element 10 used with the system of FIG. 2. The thickness of both layers 12, 14 of a same material is chosen for operation at the fundamental frequency of 1.25 MHz and second harmonic frequency of 2.5 MHz, but other frequencies can be used.

Figure 6:
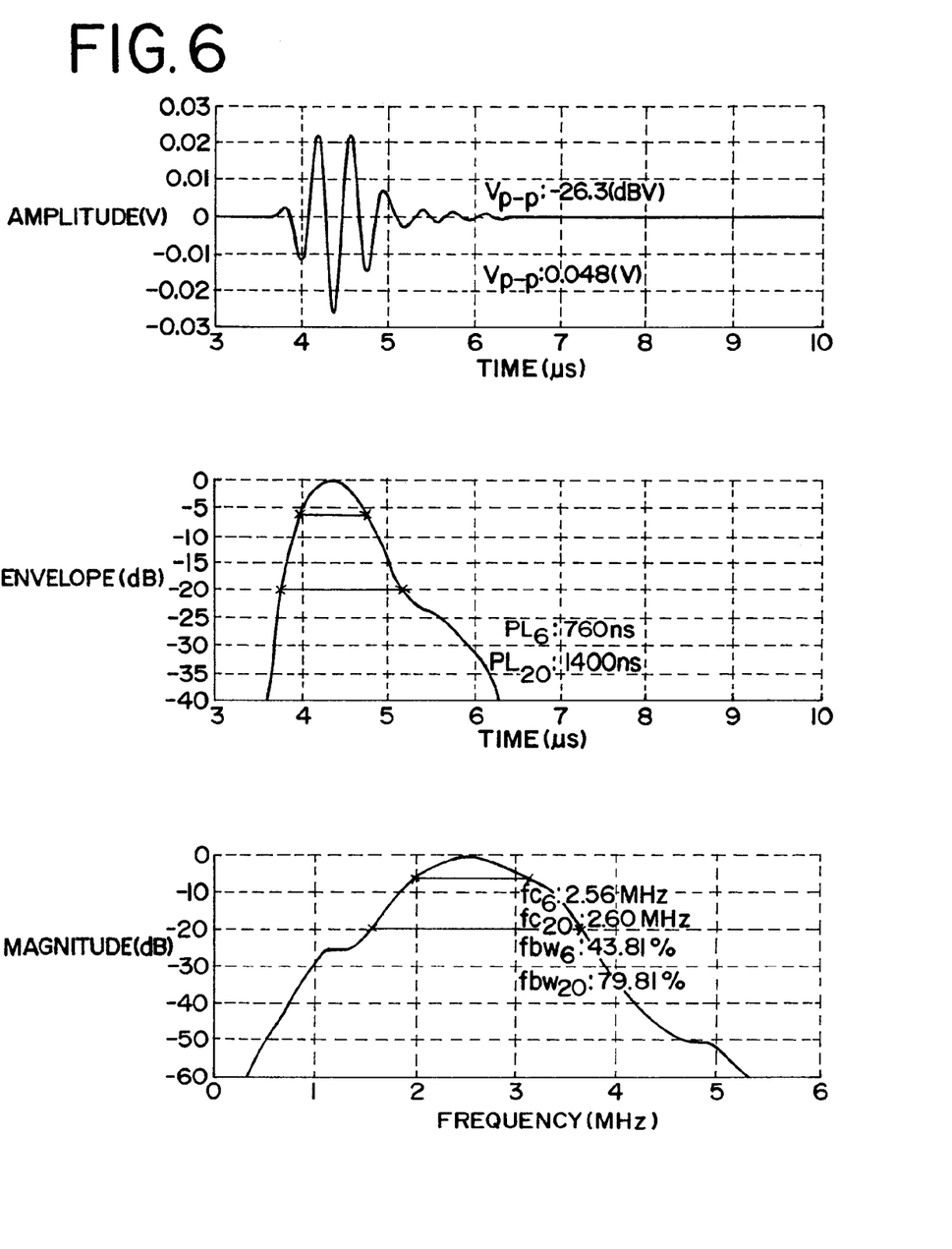
FIGS. 6–10 are graphical representations of a transducer two-way amplitude, envelope and spectral response for a multiple layer transducer of the transducer system of FIG. 2.

FIG. 6 shows a simulated two way impulse response of the element 10, waveform envelope as a function of time and spectral response of a bi-layer transducer element 10 operated at the harmonic frequency operating at 2.56 MHz. One of the receive signals is inverted for opposite polarity summation, but otherwise the amplitude and delay for both layers 12, 14 is the same.

Figure 7:
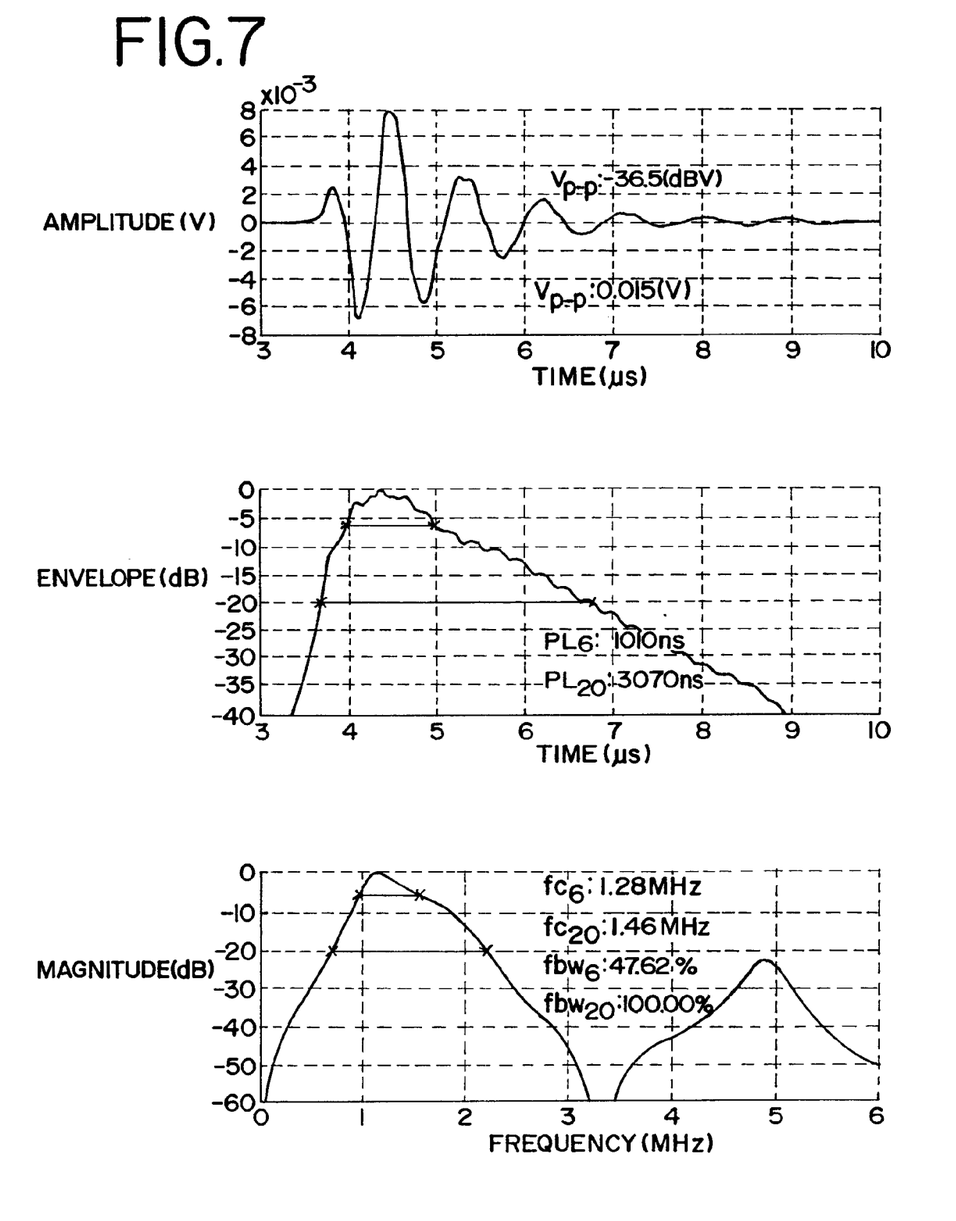

FIG. 7 shows the simulated two way impulse response waveform amplitude, waveform envelope and spectral response of the bi-layer transducer element 10 operated at the fundamental frequency of 1.28 MHz (i.e. adding signals from each layer 12, 14 on receive). The amplitude and delay for both layers 12, 14 is the same.

Figure 8:
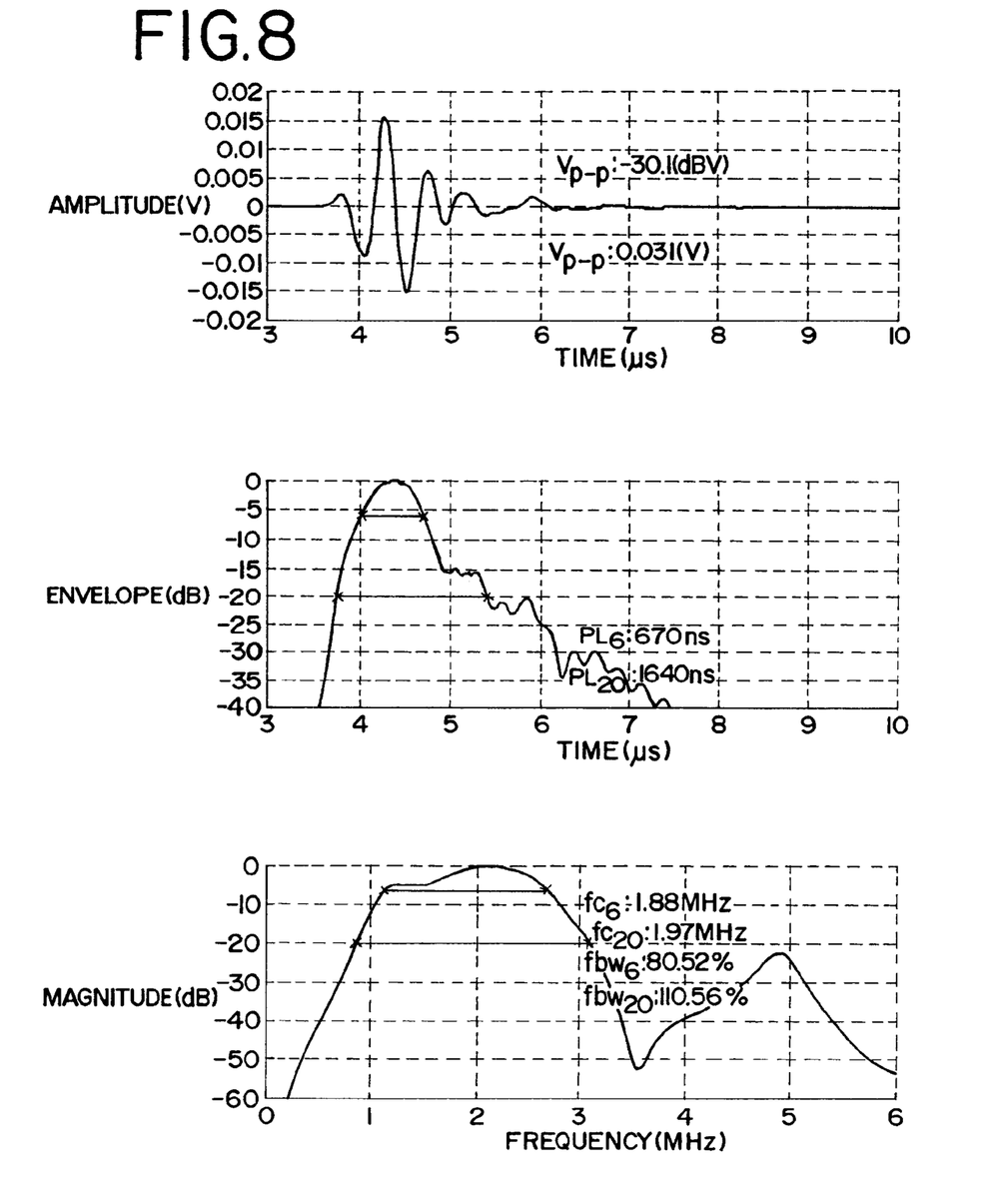

FIG. 8 shows the simulated two way impulse response waveform amplitude, waveform envelope and spectral response of the bi-layer transducer element 10 operated at the harmonic frequency with one-third wavelength delays in transmit and receive applied to the bottom layer 14 (i.e. layer adjacent the backing block 16). The amplitude is the same for both layers 12, 14 and the harmonic information is generated by applying an opposite polarity (i.e. subtraction of the received signals) to received signals from the bottom layer 14. Under this mode of operation, the transducer exhibits relatively wide bandwidth.

Figure 9:
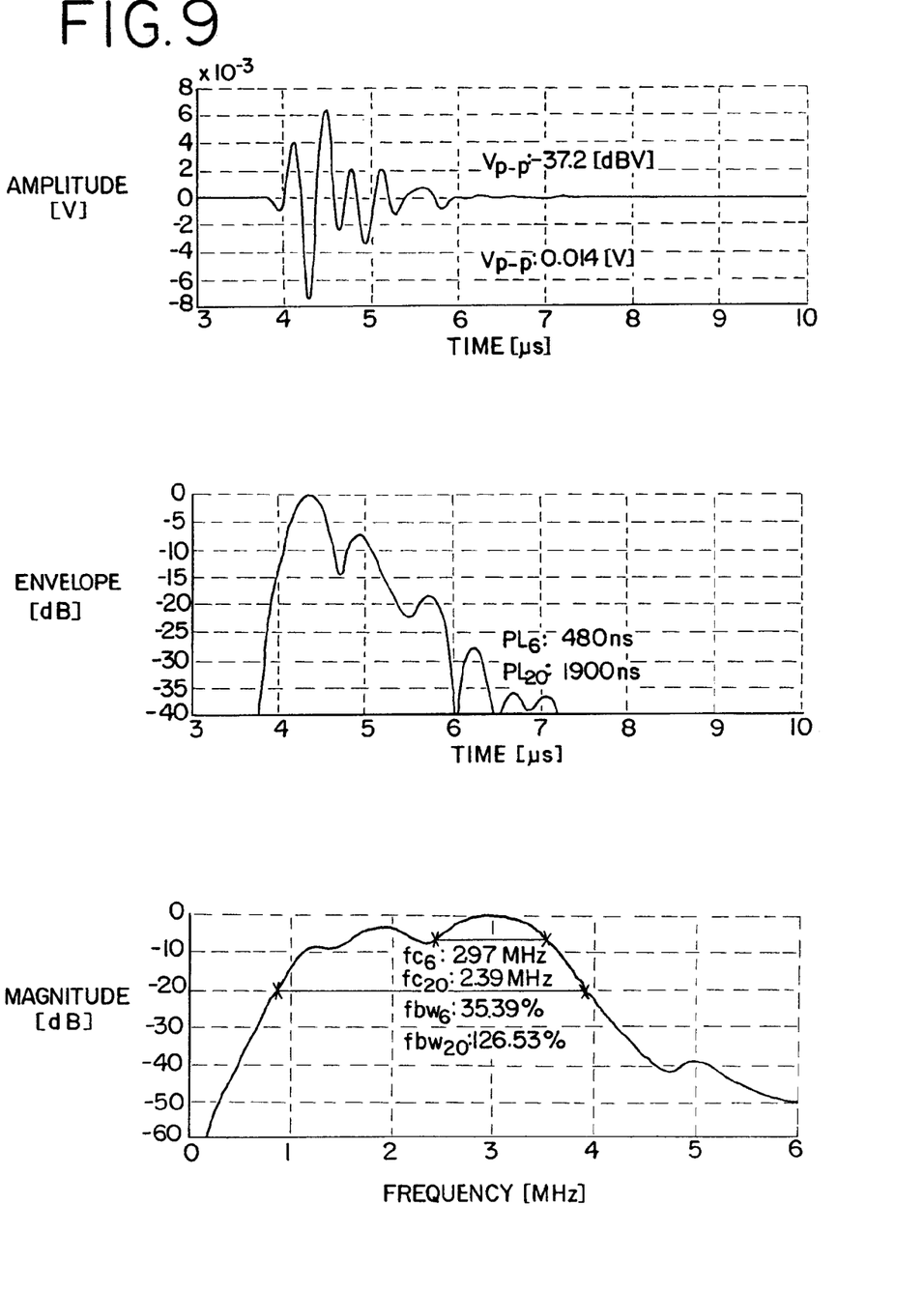

FIG. 9 shows the simulated two way impulse response waveform amplitude, waveform envelope and spectral response of the bi-layer transducer element 10 operated at the harmonic frequency with one-half wavelength delays in transmit and receive applied to the bottom layer 14 (i.e. layer adjacent the backing block 16). The amplitude is the same for both layers, and the harmonic information is generated by applying an opposite polarity (i.e. subtraction of the received signals) to received signals from the bottom layer 14.

Figure 10:
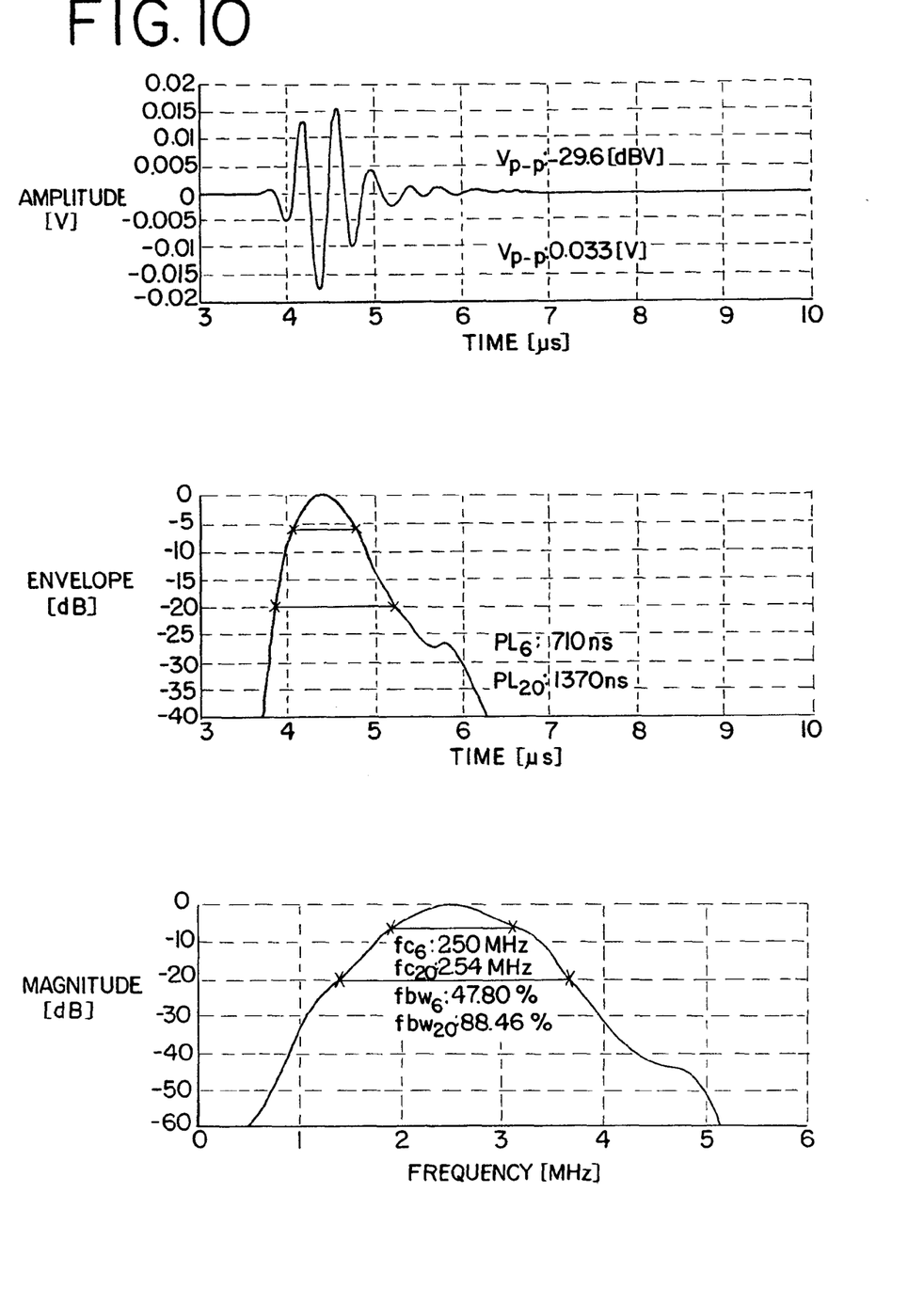

FIG. 10 shows the simulated two way impulse response waveform amplitude, waveform envelope and spectral response of the bi-layer transducer element 10 operated at the harmonic frequency with 40% reduction in amplitude in transmit and receive applied to the bottom layer 14 (i.e. layer adjacent the backing block 16). The delay is the same for both layers and the harmonic information is generated by applying an opposite polarity (i.e. subtraction of the received signals) to received signals from the bottom layer 14. A 10–15% reduction or other reductions in amplitude may provide a more desirable echo-response characteristics.

The combined information from each transducer element 10 is received by the receive beamformer 32. The receive beamformer 32 obtains information from a plurality of transducer elements 10, applies focusing delays and apodization functions and generates in-phase and quadrature or radio frequency information representing one or more locations within a scanned body.

The in-phase and quadrature or radio frequency information is filtered by the filter 34. The filter 34 isolates or passes information at the fundamental frequencies or harmonics of the fundamental transmit frequencies. Information outside of the selected band is filtered or reduced. For example, the information at fundamental transmit frequencies is filtered and information at a second harmonic band is passed or isolated by the filter 34. As another example, the information at the fundamental transmit frequencies is passed or isolated by the filter 34. The filtered information may be used in combination with other information or alone to generate an image on an ultrasound system. It is also possible to independently process separated fundamental and harmonic data and combine the information after signal detection to obtain a reduced speckle image. This compounding occurs over all or part of the image region.

Harmonic information is used for one of tissue imaging or contrast agent imaging. In tissue imaging, no additional contrast agent is added to the target during an imaging session. Only the characteristics of a tissue, including blood or other fluids, are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the imaging session. Tissue harmonic images may provide a particularly high spatial resolution as a function of the echo generated from the tissue at harmonic frequencies. In particular, there may often be less clutter in the near field. Additionally, because the transmit beam is generated using the fundamental frequency, the transmit beam profile may be less distorted by a specific level of tissue-related phase aberration than would a transmit beam formed using signals transmitted directly at the second harmonic.

Imaging may be aided by the introduction of contrast agents. In contrast agent harmonic imaging, any one of a number of well known ultrasound contrast agents, such as microspheres, are added to the target or patient in order to enhance the nonlinear response of the tissue or fluid. The contrast agents radiate ultrasonic energy at the harmonic of an insonifying energy at fundamental frequencies.

Using the transducer systems shown in FIG. 1 or 2 or other transducer systems described herein, optimal information is generated for imaging at a selected frequency. For harmonic imaging, the systems may be used in combination with other harmonic imaging techniques, such as techniques utilizing different transmit or receive processing. For example, the transmit waveform output by each of the transducer elements 10 is shaped as a function of the applied electrical transmit waveforms to minimize energy at the second harmonic or any harmonic. The output transmit waveform from each element 10 may be predistorted to account for any propagation or system nonlinearities. As another example, delays and apodization from one element 10 to another element 10 are altered to provide a line focus or a more spread beam. The relative phasing associated with each beam transmitted may alternate as a function of scan line and then data from different beams is combined. Other harmonic imaging techniques may also be used.

Figure 4:
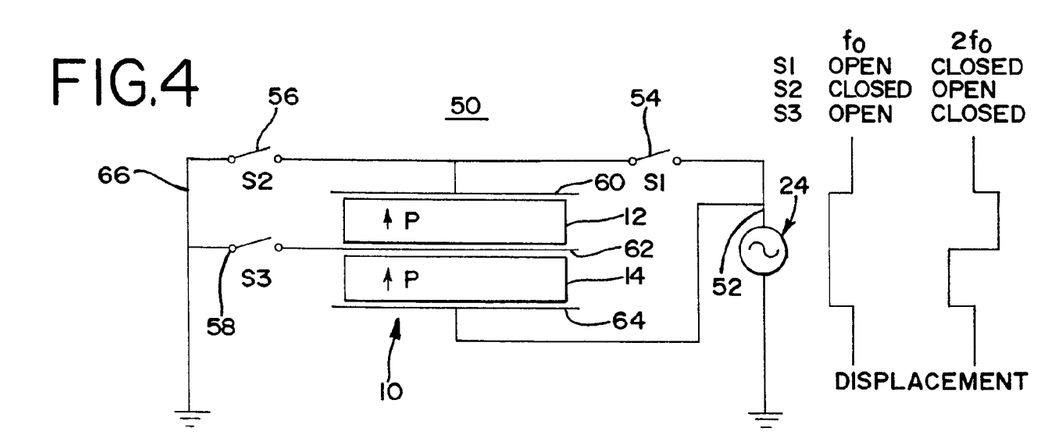
FIG. 4 is a representation of one embodiment of a multiplexer arranged for a bi-layer transducer element.
Figure 5:
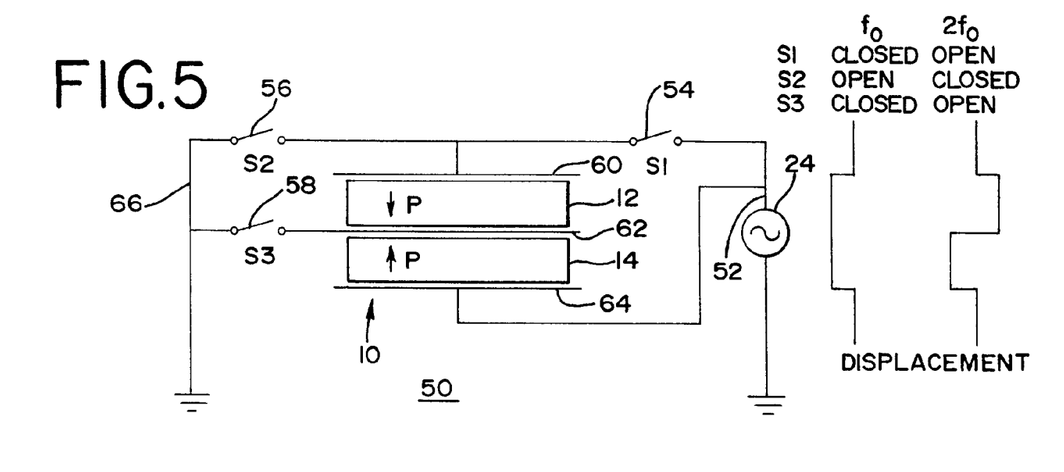
FIG. 5 is a representation of another embodiment of a multiplexer arranged for a bi-layer transducer element.

A multiplexer connecting the bi-layer transducer element 10 with the transmit and receive signal paths may further provide for selectable operation of the bi-layer transducer element 10 at different frequencies. FIGS. 4 and 1 show multiplexers 50 for selecting operation at a fundamental or a second harmonic of the fundamental frequency. These switching schemes enable dual frequency operation of the transducer with two system channels connected to one transducer element using electrodes 60 and 64, or, by controlling the switches, the transducer is configured such that one system channel 24 is connected to the transducer element 10. In this later mode of operation, the default frequency can be the fundamental or harmonic depending on the switch configuration. Both of the multiplexers 50 of FIGS. 4 and 5 are used with a single system channel 52 for both layers 12, 14 of the element 10, but a separate system channels may be provided for each of the layers 12, 14. The multiplexers 50 include three switches 54, 56 and 58 for each element 10. The switches 54, 56, 58 comprises separate transistors or other switches on a same or different semiconductor chip. In one embodiment, the switches 54, 56 and 58 for a plurality of bi-layer transducer elements 10 are incorporated on one semiconductor chip.

For the dual frequency mode of operation, the connection from the electrode 65 is reconnected to a separate system channel. Similarly, the signal from the electrode 60 is connected to the second system channel. The middle electrode 62 is connected to ground via the switch 58. For the single system channel mode of operation the connections are as shown in FIGS. 4 and 5.

The first switch 54 is selectively connectable between a top electrode 60 of the top layer 12 and the signal path 52, such as a transmit path including the transmitter 24 and receive signal path. The second switch 56 is selectively connectable with a different path 66, such as a ground connection path or a path connected to a source of potential, and the top electrode 60. The third switch 58 is selectively connectable with the different path 66 and an middle electrode 62 between the two layers 12, 14. A bottom electrode 64 connects with the signal path 52. In alternative embodiments, the first and second switches are connectable with a bottom electrode 64 or a center electrode 62, and the third switch 58 is connectable with a different electrode.

FIG. 4 shows the poling of the layers 12, 14 in a same direction. For transmit or receive operation at a fundamental frequency, the first and third switches 54, 58 are opened, and the second switch 56 is closed. For receive operation at a harmonic of the fundamental frequency, the first and third switches 54, 58 are closed, and the second switch 56 is open. If both layers 12, 14 are compressed or rarified, operation at a lower or fundamental frequency is provided. If both layers 12, 14 are in opposite states, operation at a higher or higher order harmonic frequency is provided.

FIG. 5 shows the poling of the layers 12, 14 in opposite directions. For transmit or receive operation at a fundamental frequency, the first and third switches 54, 58 are closed, and the second switch 56 is open. For receive operation at a harmonic of the fundamental frequency, the first and third switches 54, 58 are open, and the second switch 56 is closed.

The poling arrangements provide different default operating frequencies of the bi-layer transducer when operated in the single system channel mode. For the states where the second switch 56 is closed and the first and third switches 54, 58 are open, a capacitance C for the bi-layer transducer element 10 results. For the other state where the second switch 56 is open and the first and third switches 54, 58 are closed, the capacitance is 4C. The dielectric cross-section doubles in this other state while the effective thickness is half of the opposite state. For a given capacitance, doubling the frequency of operation reduces the impedance by half. For the common polarization of FIG. 4, the impedance of the bi-layer transducer element 10 at the fundamental frequency is Z and at the second harmonic frequency is Z/8. For the opposing polarization of FIG. 5, the impedance of the bi-layer transducer element 10 at the fundamental frequency is Z/4 and at the second harmonic frequency is Z/2. The opposing polarization of FIG. 5 provides a more constant impedance for operation with the ultrasound system.

Where a single channel connects with a bi-layer transducer element 10, altering signals to or from one layer relative to another layer is performed by circuitry (e.g. processing circuits 28, 29) between the switches 54, 56 and 58 and the layers 12, 14. Alternatively, no layer relative delay or amplitude alteration is performed, or separate channels are provided for each layer 12, 14. A single channel structure reduces hardware and/or increases the number of system channels available for separate transducer elements 10 of an array.

The broad bandwidth provided by any of the embodiments discussed above may allow the transducer system to be used with new or previously difficult to implement transmit or receive techniques. For example, the symbol rate in an acoustic code for a coded excitation is limited by the ability of the transducer to provide sufficient bandwidth. The transducer system described herein may be used for coded excitations, such as disclosed in U.S. Pat. No. 5,984,869, the disclosure of which is herein incorporated by reference.

While the invention has been described above by reference to various embodiments, it will be understood that many changes and modifications can be made without departing from the scope of the invention. For example, a third or fourth layer may be used for each transducer element. Different independent processes may be provided for information associated with either transmit or receive events for each layer. The layer dimensions (especially thickness) for each of the layers may be different. One or more of the piezoelectric layers may vary in thickness, such as the plano-concave layers described in U.S. Pat. Nos. 5,415,175 and 5,438,998, the disclosures of which are incorporated herein by reference. Additionally, the concepts may extend to 1.5 and 2D arrays. Furthermore, not all the elements in the array need to contain multiple piezoelectric layers. For example, in a 1.5D array, only the center elements have multiple piezoelectric layers. Since the bi-layer transducer provides constructive summation of waveforms, only one-half a peak voltage is required to provide a unity voltage output. Accordingly, the bi-layer transducer is advantageously used with a battery powered ultrasound system, such as a handheld, carried or mobile ultrasound system.

It is therefore intended that the foregoing detailed description be understood as an illustration of the presently preferred embodiments of the invention, and not as a definition of the invention. It is only the following claims, including all equivalents that are intended to define the scope of the invention.

What is claimed is:

1. An ultrasound transducer element system for imaging at one or more frequencies, the system comprising:
   a first layer of a transducer element;
   a second layer of the transducer element, the second layer stacked with the first layer along a range dimension; and
   first and second receive beamformer channels connected with the first and second layers, respectively, the first receive beamformer channel separate from the second receive beamformer channel.

2. The ultrasound system of claim 1 wherein:

the first layer comprises solid piezoelectric material; and the second layer comprises a piezo-composite material.

3. The system of claim 2 wherein the first layer is adjacent a backing block and the second layer is adjacent an emitting face of the element.

4. The system of claim 1 further comprising:

wherein the first and second receive beamformer channels are operable to independently process information during a receive event.

5. The system of claim 1 wherein the second receive beamformer channel comprises a delay, the delay operable to delay a waveform of the second layer relative to a waveform of the first layer.

6. The system of claim 1 wherein the second receive beamformer channel comprises an amplifier, the amplifier operable to amplify a waveform of the second layer relative to a waveform of the first layer.

7. The system of claim 1 further comprising:

first and second transmit beamformer channels separately connected with the first and second layers, respectively;

wherein the first and second transmit beamformer channels are operable to independently generate transmit waveforms.

8. The system of claim 1 wherein the second receive beamformer channel comprises a filter operable to alter a received signal from the second layer relative to a received signal from the first layer, the alteration a function of an acoustic transfer characteristic of the second layer.

9. The system of claim 1 further comprising a matching layer adjacent the second layer, the matching layer varying in an impedance characteristic along one dimension.

10. The system of claim 1 further comprising:

a first electrode adjacent the first layer, a second electrode adjacent the second layer and a third electrode between the first and second layers; and a multiplexer having three switches each connectable with one of two of the first, second and third electrodes.

11. The system of claim 1 wherein the first layer has a thickness that varies along at least one dimension.

12. A method for operating a bi-layer transducer element, the method comprising:

(a) transferring energy in a first layer;

(b) transferring energy in a second layer;

(c) altering a first signal associated with the first layer relative to a second signal associated with the second layer, the alteration a function of a difference in acoustic transfer characteristics of the first and second layers; and (d) determining a resonance frequency of the element as a function of (c) with first and second separate receive beamformation channels for the first and second layers, respectively.

13. The method of claim 12 wherein (a) comprises transferring energy in a solid piezoelectric material, and (b) comprises transferring energy in a piezo-composite material.

14. The method of claim 12 wherein (a) and (b) comprise transferring acoustic energy in response to at least one transmit waveform; and (c) comprises altering at least one of amplitude and delay of the first signal relative to the second signal.

15. The method of claim 12 wherein (a) and (b) comprise transferring acoustic energy in response to at least one received acoustic signal; and (c) comprises altering at least one of amplitude and delay of the first signal relative to the second signal.

16. The method of claim 12 further comprising:

(e) increasing a bandwidth of the transducer element as a function of an impedance variation of a matching layer along one dimension, the matching layer adjacent the second layer.

17. The method of claim 12 further comprising:

(e) selectably connecting a first electrode of the bi-layer transducer element to a first path;

(f) selectably disconnecting the first electrode from a second path; and (g) selectably connecting or disconnecting a second electrode of the bi-layer transducer element to one of the first and second paths.

18. An ultrasound transducer element of a transducer array for imaging at one or more frequencies, the transducer element comprising:

a first layer; and a second layer stacked with the first layer along a range dimension; and a matching layer adjacent the second layer, the matching layer varying in an impedance characteristic along one dimension; and wherein the matching layer matches a lower frequency at an edge portion along the elevation dimension and matches a higher frequency at a center portion, the higher frequency a harmonic of the lower frequency.

19. The element of claim 18 wherein the matching layer varies in thickness along an elevation dimension.

20. The element of claim 18 wherein the first layer comprises a solid piezoelectric material and the second layer comprises a piezo-composite material.

21. The element of claim 18 further comprising:

a first electrode adjacent the first layer, a second electrode adjacent the second layer and a third electrode between the first and second layers; and switches connected to the first, second and third electrodes for selectable operation under a dual frequency mode of operation and a single resonance frequency mode of operation.

22. An ultrasound transducer element of a transducer array for imaging at one or more frequencies, the transducer element comprising:

a first layer; and a second layer stacked with the first layer along a range dimension; and a matching layer adjacent the second layer, the matching layer varying in an impedance characteristic along one dimension; and wherein the matching layer comprises at least two different materials, a density of the first material greater at edge portions than at a center portion of the matching layer and a density of the second material greater at the center portion than at the edge portions of the matching layer.

23. An ultrasound transducer element of a transducer array for imaging at one or more frequencies, the transducer element comprising:

a first layer; and a second layer stacked with the first layer along a range dimension; and a matching layer adjacent the second layer, the matching layer varying in an impedance characteristic along one dimension; and wherein the matching layer is patterned along an elevation dimension, the patterning providing one of apertures, divots and indentions.

24. A method for operating a bi-layer transducer element, the method comprising:
(a) transferring energy in a first layer;
(b) transferring energy in a second layer;
(c) increasing a bandwidth of the transducer element as a function of an impedance variation of a matching layer along one dimension, the matching layer adjacent the second layer;
(d) matching an impedance for a lower frequency at an edge of the element; and
(e) matching an impedance for a higher frequency at a center of the element, the higher frequency being a harmonic of the lower frequency.

25. The method of claim 24 wherein (c) comprises varying a thickness of the matching layer along an elevation dimension.

26. The method of claim 24 further comprising:
(d) matching an impedance for a lower frequency at an edge of the element; and
(e) matching an impedance for a higher frequency at a center of the element, the higher frequency being a harmonic of the lower frequency.

27. The method of claim 24 further comprising:
(d) selectably connecting a first electrode of the bi-layer transducer element to a first path;
(e) selectably disconnecting the first electrode from a second path; and
(f) selectably connecting or disconnecting a second electrode of the bi-layer transducer element to one of the first and second paths.

28. A method for operating a bi-layer transducer element, the method comprising:
(a) transferring energy in a first layer;
(b) transferring energy in a second layer;
(c) increasing a bandwidth of the transducer element as a function of an impedance variation of a matching layer along one dimension, the matching layer adjacent the second layer;
wherein (c) comprises varying a density of a first matching layer material relative the density of a second matching layer material, the density of the first matching layer material being greater at edge portions of the element along an elevation dimension.

29. A method for operating a bi-layer transducer element, the method comprising:
(a) transferring energy in a first layer;
(b) transferring energy in a second layer;
(c) increasing a bandwidth of the transducer element as a function of an impedance variation of a matching layer along one dimension, the matching layer adjacent the second layer;
wherein (c) comprises patterning the matching layer, the patterning providing one of apertures, divots and indentions.

30. A method for operating a bi-layer transducer element, the method comprising:
(a) transferring energy in a first layer;
(b) transferring energy in a second layer;
(c) increasing a bandwidth of the transducer element as a function of an impedance variation of a matching layer along one dimension, the matching layer adjacent the second layer;
wherein the first layer comprises a solid piezoelectric material and the second layer comprises a peizo-composite material; and further comprising:
(d) altering a first signal associated with the first layer relative to a second signal associated with the second layer, the alteration a function of a difference in acoustic transfer characteristics of the first and second layers.

31. An ultrasound transducer multiplexer for connecting a bi-layer transducer element, the multiplexer comprising:
a first switch connectable between a first path and a first electrode of the bi-layer transducer element;
a second switch connectable between a second path and the first electrode; and
a third switch connectable between the second path and a second electrode of the bi-layer transducer element.

32. The multiplexer of claim 31 further comprising:
a connection between the first path and a third electrode of the bi-layer transducer element.

33. The multiplexer of claim 31 wherein the second path comprises a ground connection and the first path comprises a signal path.

34. The multiplexer of claim 31 wherein the bi-layer transducer element is responsive to a lower frequency when the first and third switches are closed and the second switch is open, the bi-layer transducer element is responsive to a higher frequency when the first and third switches are open and the second switch is closed, the higher frequency a harmonic of the lower frequency.

35. The multiplexer of claim 31 wherein the bi-layer transducer element comprises a first layer of solid piezoelectric material and a second layer of piezo-composite material, the first electrode on the second layer, the second electrode between the first and second layers and the third electrode on the first layer.

36. The multiplexer of claim 31 wherein the bi-layer transducer element comprises a matching layer varying in an impedance characteristic along an elevation dimension.

37. A method for operating a bi-layer transducer element, the method comprising:
(a) transferring energy in a first layer of the bi-layer transducer element;
(b) transferring energy in a second layer of the bi-layer transducer element; and
(c) selecting connections between at least two electrodes and two paths for (a) and (b), a frequency of operation responsive to the selection.

38. The method of claim 37 wherein (c) comprises:
(c1) connecting a first electrode of the bi-layer transducer element to a signal path;
(c2) disconnecting the first electrode from a ground connection; and
(c3) connecting a second electrode of the bi-layer transducer element to the ground connection;
wherein the frequency of operation comprises a lower frequency than associated with (c1) comprising disconnecting, (c2) comprising connecting and (c3) comprising disconnecting.

39. The method of claim 37 wherein (c) comprises:
(c1) disconnecting a first electrode of the bi-layer transducer element to a signal path;
(c2) connecting the first electrode from a ground connection; and
(c3) disconnecting a second electrode of the bi-layer transducer element to the ground connection;

wherein the frequency of operation comprises a higher frequency than associated with (c1) comprising connecting, (c2) comprising disconnecting and (c3) comprising connecting.

40. The method of claim 37 wherein (c) comprises:
(c1) connecting a first electrode of the bi-layer transducer element to a signal path;
(c2) disconnecting the first electrode from a ground connection; and
(c3) connecting a second electrode of the bi-layer transducer element to the ground connection;
wherein the frequency of operation comprises a higher frequency than associated with (c1) comprising disconnecting, (c2) comprising connecting and (c3) comprising disconnecting.

41. The method of claim 37 wherein the first layer comprises a solid piezoelectric material and the second layer comprises a peizo-composite material; and further comprising:
(d) altering a first signal associated with the first layer relative to a second signal associated with the second layer, the alteration a function of a difference in acoustic transfer characteristics of the first and second layers.

42. The method of claim 37 further comprising:
(d) increasing a bandwidth of the transducer element as a function of an impedance variation of a matching layer along an elevation dimension, the matching layer adjacent the second layer.

* * * * *